(12) United States Patent
Ren et al.

(10) Patent No.: US 8,172,460 B2
(45) Date of Patent: May 8, 2012

(54) CT SCANNING DEVICE

(75) Inventors: Jingyi Ren, Beijing (CN); Yongli Pu, Beijing (CN)

(73) Assignee: GE Medical Systems Global Technology Company LLC, Waukesha, WI (US)

( * ) Notice: Subject to any disclaimer, the term of this patent is extended or adjusted under 35 U.S.C. 154(b) by 70 days.

(21) Appl. No.: 12/629,993

(22) Filed: Dec. 3, 2009

(65) Prior Publication Data

US 2010/0142669 A1 Jun. 10, 2010

(30) Foreign Application Priority Data

Dec. 4, 2008 (CN) .......................... 2008 1 0181668

(51) Int. Cl.
*H05G 1/02* (2006.01)
(52) U.S. Cl. .......................................... 378/195; 5/601
(58) Field of Classification Search ................ 378/4, 17, 378/20, 193, 195–197, 208, 209; 5/601
See application file for complete search history.

(56) References Cited

U.S. PATENT DOCUMENTS

| | | | |
|---|---|---|---|
| 4,797,008 A | 1/1989 | Helbig et al. | |
| 4,928,292 A | 5/1990 | Zupancic et al. | |
| 5,034,970 A * | 7/1991 | Yahata et al. | 378/20 |
| 5,071,264 A | 12/1991 | Franke et al. | |
| 5,109,397 A | 4/1992 | Gordon et al. | |
| 5,272,776 A | 12/1993 | Kitamura | |
| RE36,415 E | 11/1999 | McKenna | |
| 6,337,894 B1 | 1/2002 | Tybinkowski et al. | |
| 6,810,103 B1 | 10/2004 | Tybinkowski et al. | |
| 2005/0195944 A1 * | 9/2005 | Bartels et al. | 378/195 |
| 2009/0034887 A1 | 2/2009 | Fujikawa et al. | |

* cited by examiner

*Primary Examiner* — Jurie Yun
(74) *Attorney, Agent, or Firm* — Armstrong Teasdale LLP

(57) ABSTRACT

A CT scanning device includes a scanning gantry, a supporting means for a scanning table, and a supporting base for fixing and supporting the scanning gantry. The scanning gantry is configured to scan a subject and to collect scanning data. The supporting means supports the scanning table, and is mounted on the supporting base and located between the scanning gantry and the supporting base.

19 Claims, 5 Drawing Sheets

CT SCANNING DEVICE

CROSS REFERENCE TO RELATED APPLICATIONS

This application claims the benefit of Chinese Patent Application No. 200810181668.5 filed Dec. 4, 2008, which is hereby incorporated by reference in its entirety.

BACKGROUND OF THE INVENTION

The embodiments described herein relate to a medical scanning technique, and in particular to a scanning device of a computerized tomography system (hereinafter referred to as CT).

The scanning gantry, scanning table and table support in the scanning device of the existing CT system are completely separated from one another, as shown in FIG. 1. Such separated scanning gantry, scanning table and its support result in a large volume and thus require a large space for mounting on both width and length, meanwhile, they also cost much, so they either cannot meet the requirement of hospitals that only have small spaces for mounting or cost too much for hospitals that have few patients. In addition, the table of the existing CT scanning device is supported by a crossbeam, and during scanning, the scanning table will sag due to the weight of the patient, so the effect of scanning will be affected.

BRIEF DESCRIPTION OF THE INVENTION

The embodiments described herein provide a CT scanning device having a closely-combined scanning gantry and scanning table, which takes a relatively small space and costs low.

The CT scanning device includes a scanning gantry, a supporting means for the scanning table and a supporting base for fixing and supporting the scanning gantry. The scanning gantry scans a subject and collects the scanning data; the supporting means supports the scanning table; and the supporting means is mounted on the supporting base and located between the scanning gantry and the supporting base.

The CT scanning device further comprises a bearing bracket for fixing and mounting the scanning gantry. Said scanning gantry is mounted on the supporting base through the bearing bracket, and a connection point between the bearing bracket and the supporting base forms the tilting and wiggling point of the scanning gantry, around which the scanning gantry can tilt and wiggle.

There are two tilting and wiggling points, which are respectively located at the left and right side under the rotating center of the scanning gantry. This design makes the maximum width of the gantry not over the gantry rotation diameter, which is the minimum width of scanning gantry.

The supporting means surrounds and crosses the scanning gantry from back and forth. The supporting means at both sides of the bore of the scanning gantry are respectively connected to the supporting base at the same side therewith through two parallel connecting linkages. The connection points between the connecting linkages and the supporting means and supporting base are connected by bearings.

There is a driving connecting bar connecting the bearing bracket and one of the connecting linkages, and the connection points between said driving connecting bar and the bearing bracket and the connecting linkage are connected by bearings.

The connecting line between the tilting and wiggling point and the connection point of the driving connecting bar and the bearing bracket passes through the rotating center of the scanning gantry and is parallel to the connecting linkage.

The connecting line between two connection points between said two connecting linkages and the supporting base is parallel to the connecting line between two connection points between the two connecting linkages and the supporting means.

The two connection points of the two connecting linkages and the supporting means are at the same height as the rotating center of the scanning gantry.

The supporting means surrounds and crosses the scanning gantry. The supporting means at both sides of the bore of the scanning gantry are respectively connected to the bearing bracket at the same side therewith through bearings and to the supporting base at the same side therewith through connecting linkages. The two ends of the connecting linkage are respectively connected to the supporting means and the supporting base through bearings.

Wherein the line connecting the tilting and wiggling point for tilting and wiggling of the scanning gantry and the connection point between the bearing bracket and the supporting means is parallel to the connecting linkage; and the line connecting the connection point of the connecting linkage and the supporting means and the tilting and wiggling point is parallel to the line connecting the tilting and wiggling point and the connection point between the bearing bracket and the supporting base.

Wherein the connection point between the bearing bracket and the supporting base is at the same height as the rotating center of the scanning gantry.

The supporting means comprises an upper frame and a lower frame, and the bearing bracket and the connecting linkages are connected to the upper frame.

The upper frame and the lower frame of the supporting means are connected at a same side thereof through a parallelogrammic mechanism, with all connection points connected by bearings.

Said upper frame and lower frame at the same side are connected through two connecting linkages between the upper frame and the lower frame, and said upper frame, lower frame and the two connecting linkages form a parallelogram. Using the two connection points on the upper frame as axis points, the up and down movement of the lower frame can be adjusted by controlling the parallelogrammic mechanism.

The scanning table is located on the lower frame. The lower frame is also provided with rollers for supporting the scanning table; in addition, it also comprises a roller driver for driving the rollers to move so as to make the scanning table to move forward or backward.

The CT scanning device further comprises a carriage for supporting and driving the scanning table to move up and down, and said roller driver is arranged on the carriage.

The carriage is connected to a guide rail of the supporting means through a ball screw, and said ball screw drives the carriage to move up and down along the guide rail.

The carriage has a tongue at its front side. When the carriage elevates to the lowest scanning height, the tongue will be in parallel contact with the parallelogrammic mechanism, and the roller driver will drive the scanning table from onto the carriage into the supporting means. If the carriage continues to move up, the tongue will push the parallelogrammic mechanism of the supporting means to move up, thus keeping the carriage to be always in parallel contact with the parallelogrammic mechanism of the supporting means.

In the embodiments described herein, the supporting means of the scanning table is mounted on the supporting base of the scanning gantry and the bearing bracket through a parallelogrammic mechanism, and the scanning table and the scanning gantry are closely combined together. Using a scanning gantry, not only the subject is scanned and data collected, but also the scanning table/patient is supported, so it overcomes the defect in the existing design of using separated scanning gantry and scanning table to respectively scan and support the patient. Meanwhile, the tilt center of the scanning gantry is lowered, which greatly reduces the width of the scanning gantry. When the scanning gantry tilts, the parallelogrammic mechanism makes the scanning table to move with the rotating center. Such a solution of combining the supporting means of the scanning table with the scanning gantry not only reduces the sum of the maximum lengths of the scanning gantry and the scanning table, but also reduces the space required for mounting the whole CT system, and it reduces the cost, too. Moreover, the connection is established through the parallelogrammic mechanism between the upper frame and the lower frame of the supporting means of the scanning table, and said parallelogrammic mechanism extends into the scanning bore from the two sides of the scanning gantry, thus making the supporting means support the scanning table better, reducing the sag of the scanning table and improving the scanning effect.

DETAILED DESCRIPTION OF THE INVENTION

The modes of carrying out the present invention will be described below with reference to the drawings, but the invention is not limited to these modes.

Figure 1:
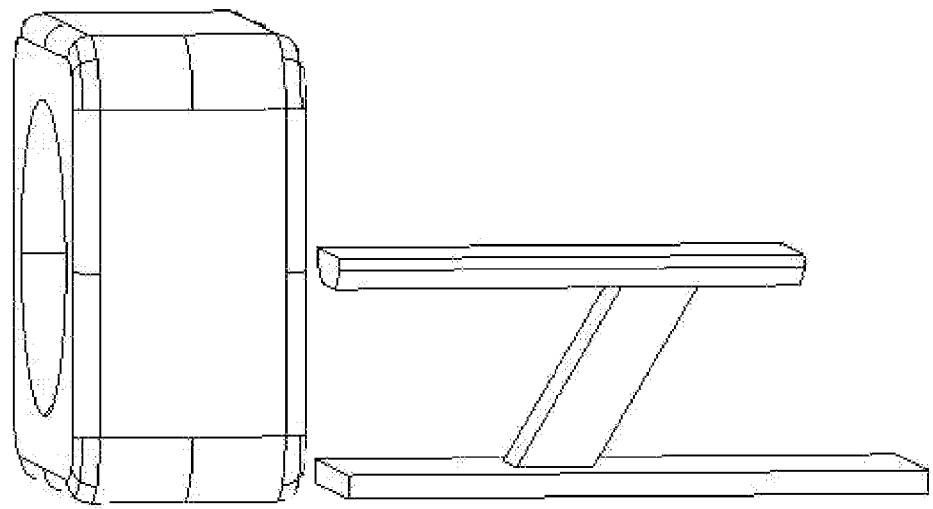
FIG. 1 is a schematic drawing of the existing separated CT scanning device.
Figure 2:
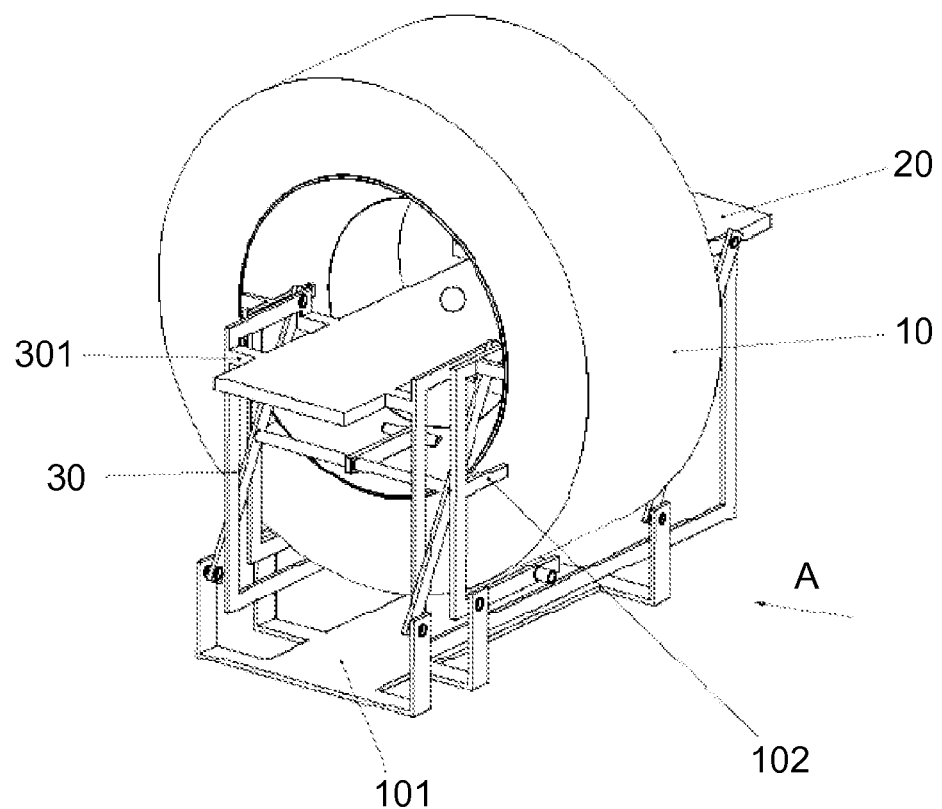
FIG. 2 is a schematic drawing of the structure of the CT scanning device of the first embodiment of the present invention.

FIG. 2 is a schematic drawing of the structure of the CT scanning device of the present invention. Said CT scanning device comprises a scanning gantry 10, a scanning table 20, a supporting means 30 connected between the scanning gantry 10 and the scanning table 20 for supporting the scanning table, and a supporting base 101 that fixes and supports the scanning gantry 10. Driven by the table driver (not shown in the figure), said scanning table 20 can move forward and backward easily on the supporting means 30 and can thereby come into and out of the center bore of the scanning gantry 10. Said scanning gantry 10 scans the subject and collects the scanned data.

Figure 3:
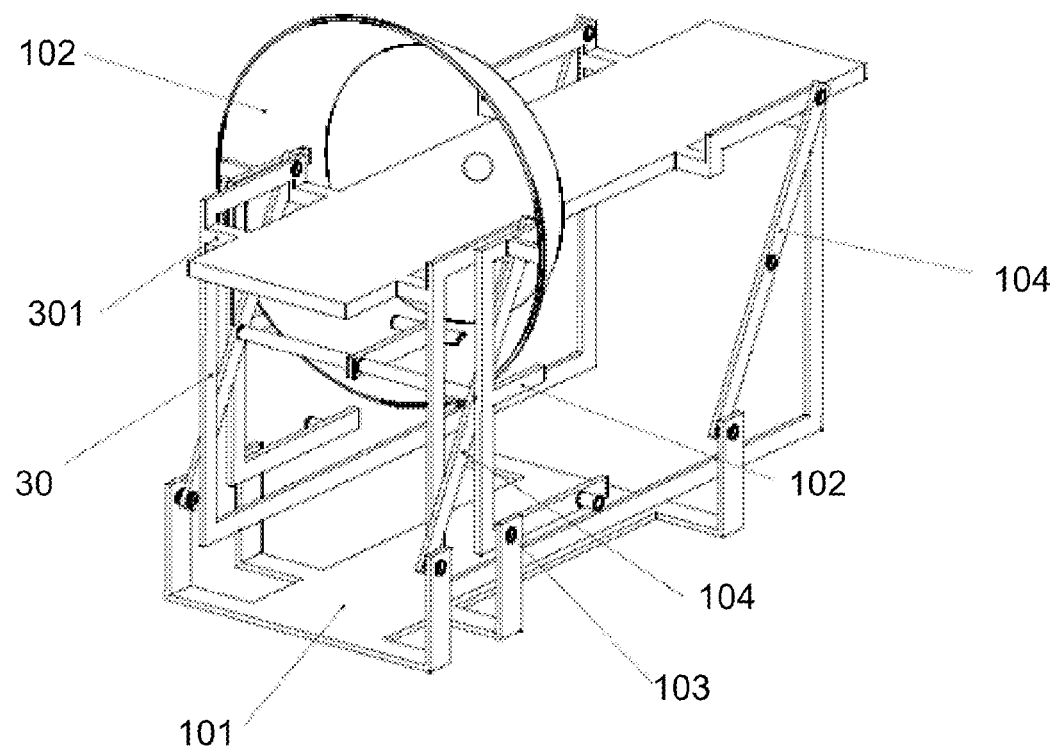
FIG. 3 is a schematic drawing of the structure of FIG. 2 with the scanning gantry removed.
Figure 4:
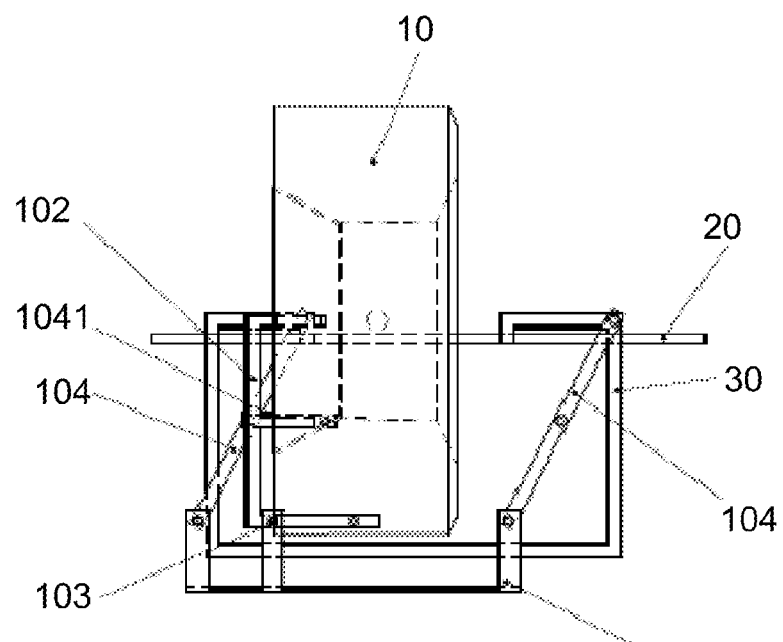
FIG. 4 is a schematic drawing of the structure viewed from direction A of FIG. 2.

With reference to FIG. 3, said scanning gantry 10 is mounted on the supporting base 101 through a bearing bracket 102, and the connection point between the bearing bracket 102 and the supporting base 101 forms a tilting and wiggling point 103 of the scanning gantry 10, and said scanning gantry 10 can tilt and wiggle around the tilting and wiggling point 103. There are two tilting and wiggling points 103, which are respectively located at outside of the lower part of the scanning gantry 10, that is, the tilting and wiggling points 103 are under the rotating center of the scanning gantry 10. Said supporting means 30 is constituted by a frame that surrounds and crosses the scanning gantry 10 back and forth, and comprises a supporting frame 301 that passes through the center bore of the scanning gantry 10 and that supports and carries the scanning table 20. The frame at both sides of the bore of the scanning gantry 10 is connected to the supporting base 101 of the scanning gantry 10 at the same side therewith through two connecting linkages 104. The two ends of said connecting linkage 104 are respectively connected to the frame of the supporting means 30 and the supporting base 101 through a bearing. With reference to FIG. 4, a driving connecting bar 1041 is connected between the bearing bracket 102 and one of the connecting linkages 104, and the two ends of the driving connecting bar 1041 are respectively connected to the bearing bracket 102 and the connecting linkage 104 through a bearing. Meanwhile, regardless of tilting state of the scanning gantry 10; the line connecting between the connection point of said driving connecting bar 1041 and the bearing bracket 102 and the tilting and wiggling point 103 for tilting and wiggling of the scanning gantry 10 will pass through the rotating center point of the scanning gantry 10 and keep parallel to the two connecting linkages 104. In this embodiment, not only the two connecting linkages 104 are parallel to each other, and the line connecting between the connection point of said driving connecting bar 1041 and the bearing bracket 102 and the tilting and wiggling point 103 for tilting and wiggling of the scanning gantry 10 is parallel to the two connecting linkages 104, but the line connecting two connection points between the two connecting linkages 104 which are located at the same side of the scanning gantry 10 and the supporting base 101 is also parallel to the line connecting two connection points between the two connecting linkages 104 and the supporting means 30, so the connecting lines between four connection points of the supporting means 30 and the supporting base 101 at both sides of the scanning gantry form a parallelogram that wiggles around the connection points.

Figure 5A:
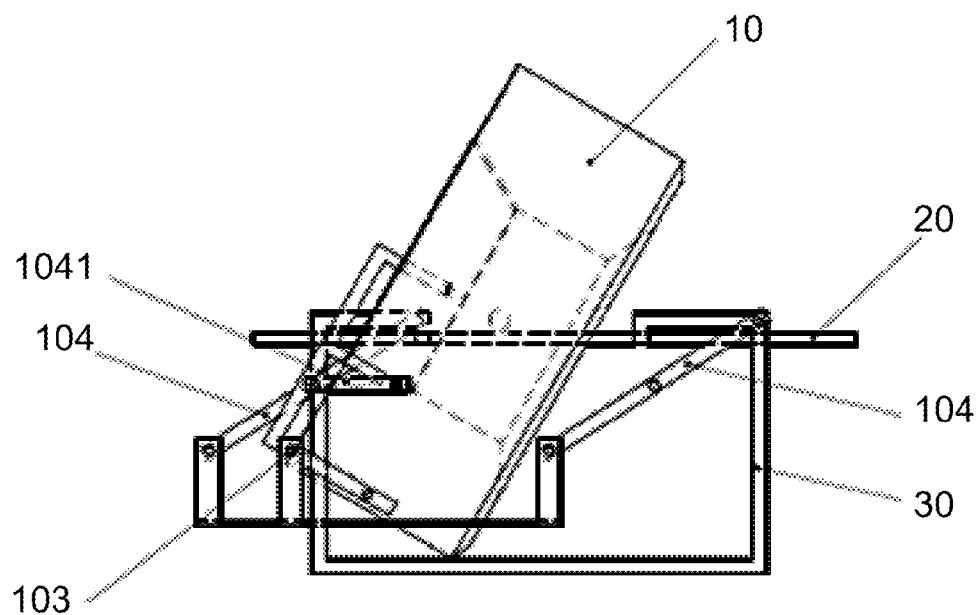
FIG. 5A and FIG. 5B are schematic drawings of the tilting and wiggling of the scanning gantry.
Figure 5B:
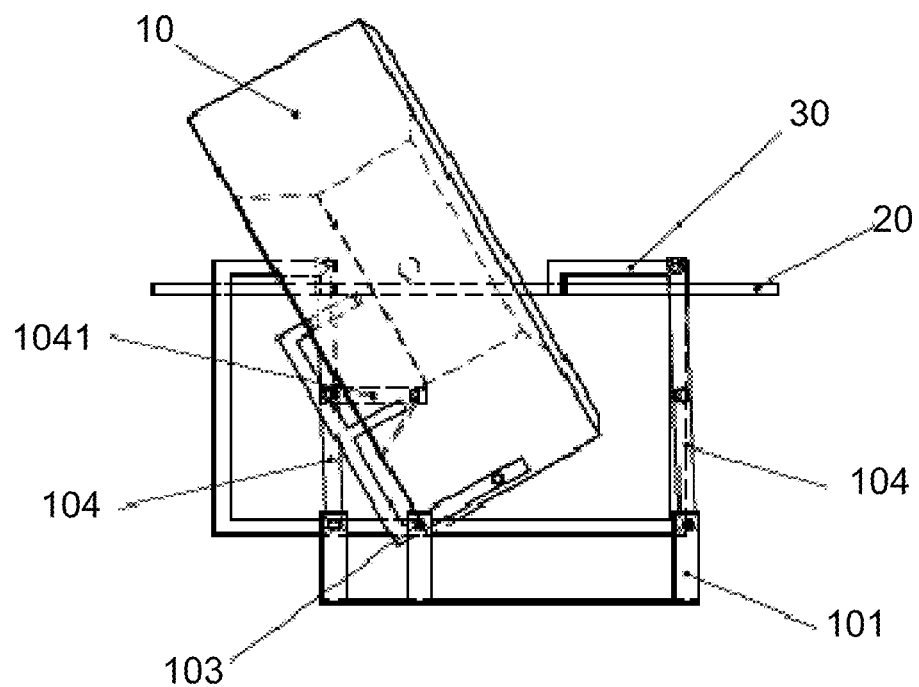

In this embodiment, the supporting means 30 for the scanning table 20 is not fixed on the ground, but it is linked and mounted through the supporting base 101, so that the supporting frame 301 of the supporting means 30 is located at the position of the scanning rotating center, and the two connection points of the two connecting linkages 104 and the supporting means 30 are at the same height as the rotating center of the scanning gantry 10. When the scanning gantry 10 tilts and wiggles around the tilting and wiggling point 103, the bearing bracket 102 connected thereto wiggles along with it, thus driving the driving connecting bar 1041 that is connected to the bearing bracket 102 to move forward or backward, and the forward-moving or backward-moving driving connecting bar 1041 in turn drives the connecting linkage 104 that is connected thereto to wiggle forward or backward, and the wiggling of said connecting linkage 104 will drive the supporting means 30 that is connected thereto and the other connecting linkage 104 to move forward and backward, which makes the supporting means 30 for the scanning table 20 wiggle with the tilting of the scanning gantry 10. As a result, when the scanning gantry 10 tilts, the scanning table 20 moves along with the rotating center, as shown in FIGS. 5A and 5B.

Figure 6:
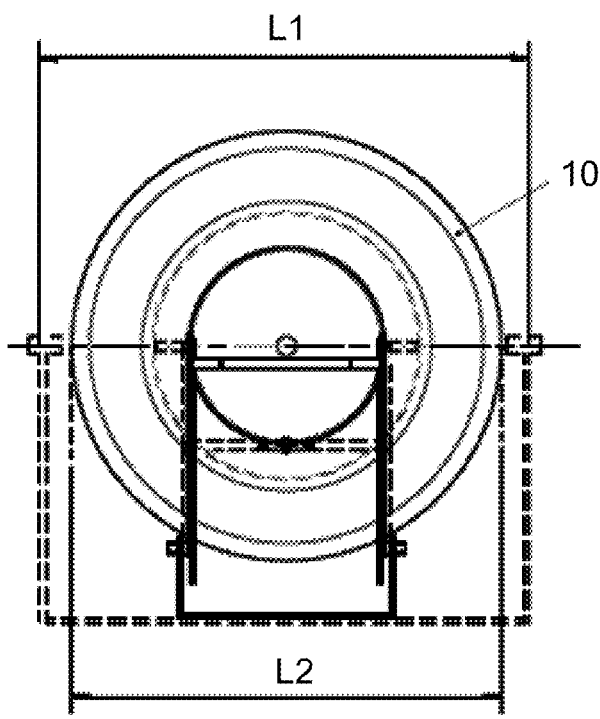
FIG. 6 is a schematic drawing of the position of the tilt axis of the scanning gantry.

In this solution, the tilting and wiggling point 103 of the scanning gantry 10 does not pass through the rotating center, instead it moves down, which not only enables the rotating center to move forward or backward along with the tilt of the scanning gantry 10 but also reduces the width of the scanning gantry 10. As shown in FIG. 6, the width of the scanning gantry 10 is determined by the length of the tilt axis of the scanning gantry 10, L1 in FIG. 6 represents the length of the existing tilt axis, and L2 represents the length of the tilt axis in this solution.

Second Embodiment

Figure 7:
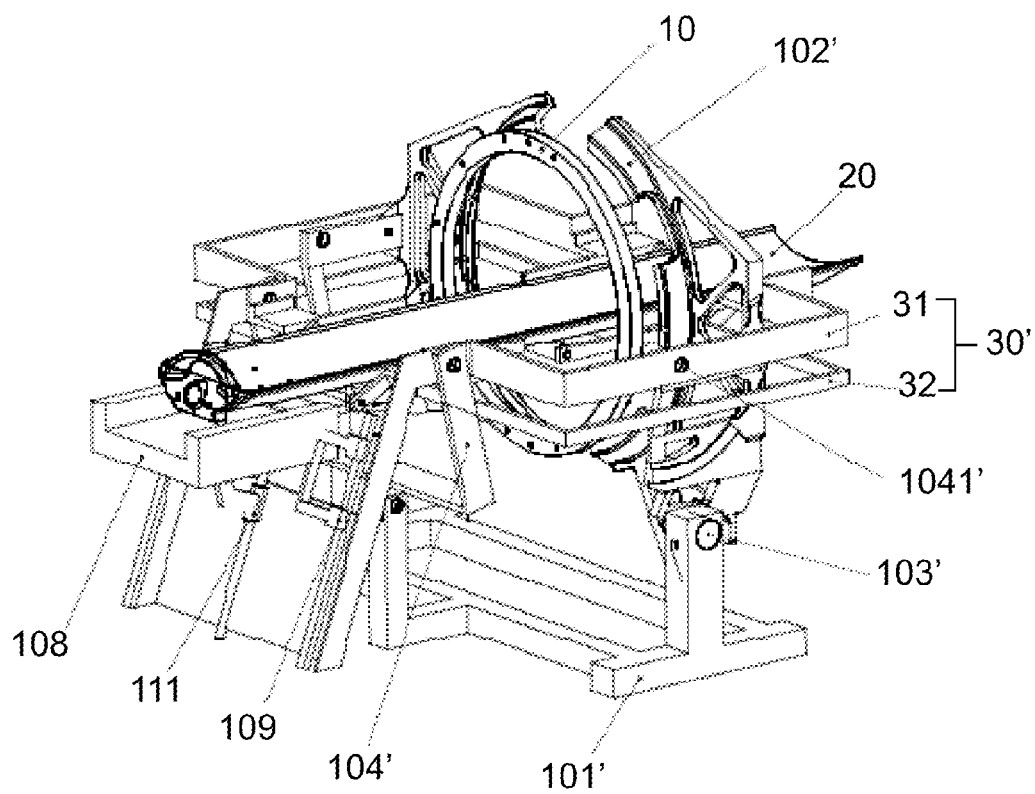
FIG. 7 and FIG. 8 are schematic drawings of the structure of the CT scanning device of the second embodiment of the present invention.

FIG. 7 is a schematic drawing of the structure of the CT scanning device of the second embodiment of the present invention. Likewise, in this embodiment, the CT scanning device also comprises a scanning gantry 10, a scanning table 20, a supporting means 30' connected between the scanning gantry 10 and the scanning table 20 for supporting the scanning table, and a supporting base 101' for fixing and supporting the scanning gantry 10. Driven by the table driver (not shown in the figure), said scanning table 20 can move forward and backward easily on the supporting means 30' and can thereby come into and out of the center bore of the scanning gantry 10. Said scanning gantry 10 scans the subject and collects the scanned data.

Figure 8:
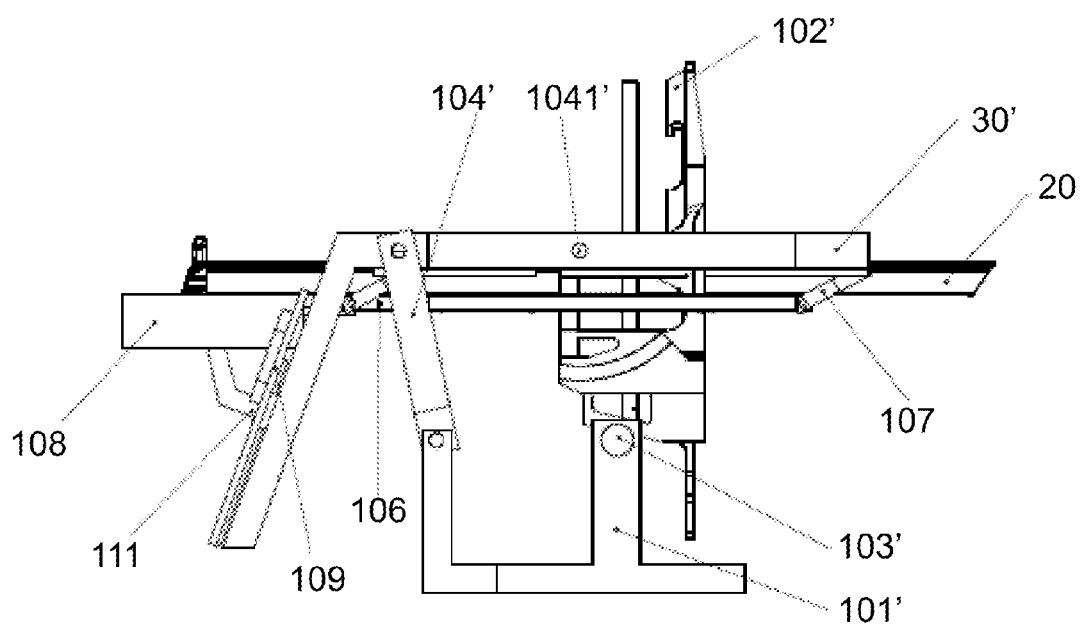

With reference to FIG. 8, said scanning gantry 10 is mounted on the supporting base 101' through a bearing bracket 102', and the connection point between the bearing bracket 102' and the supporting base 101' forms a tilting and wiggling point 103' of the scanning gantry 10, and said scanning gantry 10 can tilt and wiggle around the tilting and wiggling point 103. There are two tilting and wiggling points 103, which are respectively located at the outside of the lower part of the scanning gantry 10, that is, the tilting and wiggling points 103' are under the rotating center of the scanning gantry 10. Said supporting means 30' surrounds and crosses the scanning gantry 10. The supporting means 30' at both sides of the bore of the scanning gantry 10 are connected to the bearing bracket 102' at the same side therewith through a bearing, the connection point 1041 therebetween being at the same height with the rotating center of the scanning gantry 10, and the supporting means 30' is connected to the supporting base 101' of the scanning gantry 10 at the same side therewith through a linkage 104'. The two ends of said linkage 104' are respectively connected to said supporting means 30' and supporting base 101' through bearings, and the line connecting the tilting and wiggling point 103' and the connection point 1041' between the supporting means 30' and the bearing bracket 102' is parallel to the connecting linkage 104'. In this embodiment, the line connecting the tilting and wiggling point 103' for tilting and wiggling of the scanning gantry 10 and the connection point between the connecting linkage 104' and the supporting base 101' is parallel to the line connecting the connection point between the bearing bracket 102' and the supporting means 30' of the scanning table 20 and the connection point between the connecting linkage 104' and the supporting means 30'. Therefore, at each side of the bore of the scanning gantry 10, there are four such connection points that form a parallelogram, each being connected by a bearing.

When the scanning gantry 10 tilts and wiggles surrounding the tilting and wiggling point 103', the bearing bracket 102' connected therewith also wiggles. Since the bearing bracket 102' is one side of the above-mentioned parallelogram, its tilt and wiggle will drive the upper parallel side formed by the supporting means 30' of the scanning table 20 and another parallel side formed by the connecting linkage 104' to wiggle, thereby making the supporting means 30' of the scanning table 20 wiggle with the tilt of the scanning gantry 10. As a result, when the scanning gantry 10 tilts, the scanning table 20 moves along with the rotating center.

Likewise, in this embodiment, the tilting center of the scanning gantry 10 does not pass through the rotating center, instead it moves down. This not only enables the rotating center to move forward or backward along with the tilt of the scanning gantry 10 but also reduces the width of the scanning gantry 10.

The supporting means 30' of the scanning table 20 comprises an upper frame 31 and a lower frame 32. The upper frame 31 and the lower frame 32 are connected at the same side thereof by a parallelogrammic mechanism, and the connection points are all connected by bearings. In this embodiment, two connecting linkages 106 and 107 are connected between the upper frame 31 and the lower frame 32, and said upper frame 31, lower frame 32 and the two linkages 106, 107 form a parallelogram. Using the two connection points on the upper frame 31 as axis points, the upward and downward movement of the lower frame 32 can be adjusted by controlling said parallelogrammic mechanism. The scanning table 20 is located on the lower frame 32. The lower frame 32 also has rollers thereon (not shown in the figure) for supporting the scanning table 20. A roller driver (not shown in the figure) drives the rollers to move so as to drive the scanning table 20 to move forward or backward.

There is also included a carriage 108 on which the roller driver is arranged. Said carriage 108 is used to carry the scanning table 20 to move up and down so as to help the patient to lie down on the table. The carriage 108 can move up and down along a rail 109. When the carriage 108 reaches the lowest scanning height, a tongue (not labeled) in front of the carriage comes into contact with the lower parallel sides of the parallelogrammic mechanism, and the roller driver can easily drive the scanning table from the carriage into the supporting means 30'. If the carriage 108 continues to move up, the tongue will push the lower parallel side of the parallelogrammic mechanism of the supporting means 30' to move up, thereby keeping the carriage to be always parallel to the parallelogrammic mechanism of the supporting means 30'. When the carriage 108 and the scanning table 20 move down, a spring (not shown in the figure) between the upper and lower frames 31 and 32 of the supporting means 30' will pull the supporting means 30 back to the lowest scanning position. Since the two parallelogrammic mechanisms of the supporting means 30' extend from the two sides of the scanning gantry 10 into the center bore thereof, they can stably support the scanning table 20 and reduce the sag of the scanning table 20.

In the present invention, the carriage 108 is connected to the guide rail 109 of the supporting means 30' through a ball screw 111. Said ball screw 111 drives the carriage 108 and the scanning table 20 to move up and down. Driven by the roller driver, the four rollers on the carriage 108 drive the scanning table 20 to move forward and backward.

What is claimed is:

1. A CT scanning device, comprising:
a scanning gantry configured to tilt about a gantry rotation center, wherein said scanning gantry is configured to scan a subject and to collect scanning data;
a supporting means for a scanning table;
a supporting base for fixing and supporting the scanning gantry, wherein said supporting means supports said scanning table, and said supporting means is mounted on said supporting base and located between said scanning gantry and said supporting base; and
a bearing bracket for fixing and mounting said scanning gantry such that said scanning gantry is mounted on said supporting base through said bearing bracket and such that a connection point between said bearing bracket and said supporting base is a tilting and wiggling point of said scanning gantry around which said scanning gantry can tilt and wiggle, such that said scanning table is configured to at least one of maintain a relative position in said scanning gantry and maintain a substantially horizontal alignment during tilting of said scanning gantry.

2. The CT scanning device of claim 1, wherein said bearing bracket and said supporting base are coupled at two tilting and wiggling points respectively located at a left side and a right side under the rotating center of said scanning gantry.

3. The CT scanning device of claim 2, wherein said supporting means surrounds and crosses said scanning gantry from back and forth, and wherein said supporting means at both sides of a bore of said scanning gantry are respectively connected to said supporting base at the same side therewith through two parallel connecting linkages, such that connection points between said connecting linkages and said supporting means and said supporting base are connected by bearings.

4. The CT scanning device of claim 3, further comprising a driving connecting bar connecting said bearing bracket and one of said connecting linkages, such that connection points between said driving connecting bar and said bearing bracket and said connecting linkages are connected by bearings.

5. The CT scanning device of claim 4, wherein a connecting line between the tilting and wiggling point and the connection point of said driving connecting bar and said bearing bracket passes through the rotating center of said scanning gantry and is parallel to said connecting linkages.

6. The CT scanning device of claim 5, wherein a connecting line between two connection points of said two connecting linkages and said supporting base is parallel to the connecting line between two connection points of said two connecting linkages and said supporting means.

7. The CT scanning device of claim 6, the two connection points of said two connecting linkages and said supporting means are at a same height as the rotating center of said scanning gantry.

8. The CT scanning device of claim 2, wherein said supporting means surrounds and crosses said scanning gantry, said supporting means at both sides of a bore of said scanning gantry are respectively connected to said bearing bracket at a same side therewith through bearings and to said supporting base at the same side therewith through connecting linkages, and the two ends of said connecting linkage are respectively connected to said supporting means and said supporting base through bearings.

9. The CT scanning device of claim 8, wherein a line connecting the tilting and wiggling point for tilting and wiggling of said scanning gantry and a connection point between said bearing bracket and said supporting means is parallel to said connecting linkage, such that a line connecting the connection point of said connecting linkage and said supporting means and the tilting and wiggling point is parallel to the line connecting the tilting and wiggling point and the connection point between said bearing bracket and said supporting base.

10. The CT scanning device of claim 9, wherein the connection point of said bearing bracket and said supporting base is at the same height as the rotating center of said scanning gantry.

11. The CT scanning device of claim 10, wherein said supporting means comprises an upper frame and a lower frame, said bearing bracket and said connecting linkages are connected to said upper frame.

12. The CT scanning device of claim 11, wherein said upper frame and said lower frame are connected at a same side thereof through a parallelogrammic mechanism, and the connection points are all connected by bearings.

13. The CT scanning device of claim 12, said upper frame and said lower frame at the same side are connected through two connecting linkages between said upper frame and said lower frame, and said upper frame, said lower frame, and said two connecting linkages form a parallelogram, wherein using the two connection points on said upper frame as axis points, upward and downward movement of said lower frame is adjustable by controlling said parallelogrammic mechanism.

14. The CT scanning device of claim 13, wherein said scanning table is located on said lower frame, said lower frame comprises rollers arranged thereon for supporting said scanning table, said CT scanning device further comprising a roller driver configured to drive said rollers to move so as to make said scanning table to move forward or backward.

15. The CT scanning device of claim 14, further comprising a carriage for supporting and driving said scanning table to move up and down, and said roller drivers is arranged on said carriage.

16. The CT scanning device of claim 15, wherein said carriage is connected to a guide rail of said supporting means through a ball screw, and said ball screw drives said carriage to move up and down along said guide rail.

17. The CT scanning device of claim 16, wherein said carriage comprises a tongue along at least a portion of a front side, such that when said carriage reaches a lowest scanning height, said tongue comes into parallel contact with said parallelogrammic mechanism, and said roller driver will drive said scanning table from said carriage into said supporting means, and when said carriage continues to move up, said tongue will push said parallelogrammic mechanism of said supporting means to move up, thus keeping said carriage to be always in parallel contact with said parallelogrammic mechanism of said supporting means.

18. A CT scanning device, comprising:
a scanning gantry;
a supporting means for a scanning table;
a supporting base for fixing and supporting said scanning gantry, wherein said scanning gantry is configured to scan a subject and to collect scanning data, said supporting means supports said scanning table, and said supporting means is mounted on said supporting base and located between said scanning gantry and said supporting base; and
a bearing bracket for fixing and mounting said scanning gantry, such that said scanning gantry is mounted on said supporting base through said bearing bracket, and a connection point between said bearing bracket and said supporting base is a tilting and wiggling point of said scanning gantry, around which said scanning gantry can tilt and wiggle.

19. A method of assembling a CT scanning device, said method comprising:
providing a scanning gantry configured to scan a subject and to collect scanning data and tilt about a gantry rotation center;
positioning a supporting means with respect to a scanning table to support the scanning table;
positioning a supporting base such that the supporting means is mounted on the supporting base and located between the scanning gantry and the supporting base; and
positioning a bearing bracket such that the scanning gantry is mounted on the supporting base through the bearing bracket and a connection point between the bearing bracket and the supporting base that is a tilting and wiggling point of the scanning gantry, around which the scanning gantry can tilt and wiggle.

\* \* \* \* \*